(12) United States Patent
Sasaki et al.

(10) Patent No.: US 7,935,358 B2
(45) Date of Patent: May 3, 2011

(54) COSMETIC SKIN PREPARATION

(75) Inventors: Mitsuhiro Sasaki, Sumida-ku (JP);
Nobuo Takazawa, Sumida-ku (JP);
Masanori Tanahashi, Sumida-ku (JP);
Keiichi Fukuda, Sumida-ku (JP);
Hideki Yamauchi, Sumida-ku (JP)

(73) Assignee: Kao Corporation, Tokyo (JP)

( * ) Notice: Subject to any disclaimer, the term of this patent is extended or adjusted under 35 U.S.C. 154(b) by 496 days.

(21) Appl. No.: 11/814,695

(22) PCT Filed: Jan. 31, 2006

(86) PCT No.: PCT/JP2006/301530
§ 371 (c)(1),
(2), (4) Date: Jul. 25, 2007

(87) PCT Pub. No.: WO2006/080520
PCT Pub. Date: Aug. 3, 2006

(65) Prior Publication Data
US 2009/0035333 A1    Feb. 5, 2009

(30) Foreign Application Priority Data

Jan. 31, 2005  (JP) ................. 2005-023902
Feb. 10, 2005  (JP) ................. 2005-034598
Feb. 10, 2005  (JP) ................. 2005-034599
Feb. 10, 2005  (JP) ................. 2005-034600
Feb. 10, 2005  (JP) ................. 2005-034601

(51) Int. Cl.
*A61K 8/02* (2006.01)
*A61K 47/30* (2006.01)

(52) U.S. Cl. .................. 424/401; 514/772.3
(58) Field of Classification Search ............ 424/401
See application file for complete search history.

(56) References Cited

U.S. PATENT DOCUMENTS

| 6,713,558 B2 * | 3/2004 | Altes et al. .............. 524/806 |
| 2003/0065087 A1 * | 4/2003 | Nambu et al. ............ 524/588 |
| 2003/0108498 A1 * | 6/2003 | Stephens et al. .......... 424/63 |

FOREIGN PATENT DOCUMENTS

| JP | 2 172902 | 7/1990 |
| JP | 3-79669 | 4/1991 |
| JP | 3 197413 | 8/1991 |
| JP | 5-65212 | 3/1993 |
| JP | 5-178733 | 7/1993 |
| JP | 6-279235 | 10/1994 |
| JP | 2000-281532 | 10/2000 |
| JP | 2003 34725 | 2/2003 |
| JP | 2003-63933 | 3/2003 |
| JP | 2003 95872 | 4/2003 |
| JP | 2003 514840 | 4/2003 |
| JP | 2003-192521 | 7/2003 |

* cited by examiner

*Primary Examiner* — Sreeni Padmanabhan
*Assistant Examiner* — Timothy E Betton
(74) *Attorney, Agent, or Firm* — Oblon, Spivak, McClelland, Maier & Neustadt, L.L.P.

(57) ABSTRACT

A cosmetic skin preparation containing a porous powder which contains water absorbed therein and whose surface is coated with a binder containing a crosslinked type organopolysiloxane.

20 Claims, No Drawings

COSMETIC SKIN PREPARATION

FIELD OF THE INVENTION

The present invention relates to a cosmetic skin preparation which can continually suppress the stickiness caused by sebum while giving a cooling sensation, and can conceal unevenness of the skin.

BACKGROUND OF THE INVENTION

A large number of people at the age of late teens to early twenties are troubled by their oily skin due to excessive sebum, or are nervous about unevenness of their skin, such as the pores and the like. Feelings that these people have include aversion to or discomfort with an oily skin type, discomfort due to makeup deterioration caused by sebum or due to greasiness, discomfort due to unnatural finish of the makeup caused by high concealment, and the like. A measure that is frequently taken against excessive sebum is to remove sebum by facial cleansing. With regard to makeup deterioration or greasiness, a method of absorbing excessive sebum by pressing an oil blotting film against the skin, or alternatively, a method of spraying a skin toner in a mist form and wiping off with tissue paper is exercised upon touching up the makeup.

Furthermore, with regard to the unevenness of the skin, a method of blending body pigments in large quantities (Patent Document 1), a method of blending powders with different refractive indices (Patent Document 2), or the like is performed. However, when extender pigments are blended in large quantities, the finish becomes so thick that it looks unnatural. Also, when powders with different refractive indices are blended, depending on the dispersion state of the powders, the unevenness of the skin may become rather more clearly visible.

In addition, emulsified liquid cosmetic preparations of oil-in-water type (O/W type) or water-in-oil type (W/O type) formulation (Patent Document 3, Patent Document 4, and Patent Document 5), solid powdery cosmetic preparations of press type (Patent Document 6), or melt-filled type oily solid cosmetic preparations (Patent Document 7) are being used for these methods. However, these cosmetic preparations are insufficient in view of the sustainability of the effects, and could not sufficiently improve the skin type. Furthermore, hydrous powdery cosmetic preparations which are liquefiable by inunction (Patent Document 8) and the like have been also suggested; however, they have poor stability, and it is difficult to keep them stable under long-term storage.

[Patent Document 1] JP-A-6-279235
[Patent Document 2] JP-A-2003-63933
[Patent Document 3] JP-A-2003-192521
[Patent Document 4] JP-A-5-178733
[Patent Document 5] JP-A-3-79669
[Patent Document 6] JP-A-3-197413
[Patent Document 7] JP-A-2000-281532
[Patent Document 8] JP-A-5-65212

DISCLOSURE OF THE INVENTION

Problems to be Solved by the Invention

The present invention provides a cosmetic skin preparation having excellent storage stability, which can continually suppress the stickiness caused by sebum while giving a cooling sensation, thus mitigating the discomforts of oily skin, and can conceal unevenness of the skin.

Means to Solve the Problems

The inventors of the present invention discovered that a cosmetic skin preparation which can solve the aforementioned problems can be obtained by rendering a porous powder to absorb water, and coating the powder surface with a binder containing a crosslinked type organopolysiloxane.

The present invention is to provide a cosmetic skin preparation including a porous powder which contains water absorbed therein and has the surface of the porous powder coated with a binder containing a crosslinked type organopolysiloxane.

Effects of the Invention

The cosmetic skin preparation of the present invention can continually suppress the stickiness caused by sebum while giving a cooling sensation, thus mitigating the discomforts of oily skin, can conceal unevenness of the skin, and has excellent storage stability. Thus, the cosmetic skin preparation is suitable as a cosmetic preparation for the removal of sebum, or as a cosmetic preparation for the concealment of unevenness such as pores, wrinkles and the like.

MODE FOR CARRYING OUT THE INVENTION

Examples for the porous powder used for the present invention include organic porous powders such as polyamide, polyacrylate, polymethacrylate, styrene-divinylbenzene copolymer, cellulose and the like; metal salts of silicic acid, such as calcium silicate, aluminum silicate, barium silicate and the like; metal salts of carbonic acid, such as calcium carbonate, cobalt carbonate and the like; metal salts of tungstic acid, such as calcium tungstate and the like; metal oxides such as cobalt oxide, $\alpha$-iron oxide and the like; metal oxides such as hydrated iron oxide and the like, as well as silica (including silica gel), hydroxyapatite, lanolin powder, and the like.

Such a porous powder preferably has an average particle size of 3 to 20 μm, more preferably 5 to 15 μm, and even more preferably 10 to 15 μm. If the particles of the porous powder are too small, the spread of the cosmetic skin preparation becomes poor. If the particles of the porous powder are too large, the sensation of smearing may be felt. Furthermore, it is preferable for the porous powder that the average pore diameter of the pores present in one powder particle is 50 Å or greater.

Among them, porous silica having a water absorbability of 50 to 200 mL/100 g is preferred. The porous silica may be spherical-shaped or plate-shaped. It is more preferable to use both shapes in combination.

Here, the water absorbability is a value measured according to a two-blade mixing mode of a mechanical method (JIS K6221-1982) (the amount of water which can be absorbed by a powder), and is measured using an oil absorption measuring instrument S-410 (Frontex Corp.). The method of measurement involves calculating a torque from the torsional angle of a torsion bar, which corresponds to the mixed torque obtained when water is dropped on a powder at a rate of 4 mL/min, and taking the amount of dropped water at a torque equivalent to 70% of the maximum torque, as the water absorbability.

The porous powder (powder being in a state before absorbing water) is preferably contained in an amount of 5 to 40% by weight, and more preferably 10 to 30% by weight, based on the total composition of the cosmetic skin preparation so that the porous powder does not feel rough on the skin surface and provides a good sense of use.

According to the present invention, zinc oxide can be further contained and used in combination with the porous powder having water absorbed therein, so that absorption of sebum and gelation can occur rapidly, thereby further improving the effects of preventing greasiness or makeup deterioration.

The type of zinc oxide is not limited, as long as it is conventionally used for cosmetic preparations. The specific surface area of the zinc oxide is preferably from 10 to 100 $m^2/g$.

Zinc oxide is preferably contained in an amount of 1 to 15% by weight, and more preferably 2 to 10% by weight, based on the total composition of the cosmetic skin preparation so that the cosmetic preparation has excellent makeup sustainability, has no sensation of straining, and has a good sense of use.

According to the present invention, the cosmetic preparation can further contain a titanium oxide-containing powder. Such titanium oxide-containing powder may take a form of a complex in which titanium oxide is dispersed among a powder.

The average particle size of the titanium oxide to be included is preferably 10 to 300 nm, and more preferably 20 to 250 nm. Such titanium oxide is preferably contained in the powder in an amount of 5 to 40% by weight, and more preferably 8 to 30% by weight.

Meanwhile, the powder including such titanium oxide may be exemplified by silica, magnesium oxide, aluminum oxide, zirconium oxide, zinc oxide, chromium oxide; an organic powder of polymethyl methacrylate, a vinyl polymer and the like, with silica being more preferred.

The titanium oxide-containing powder may be either a porous powder or a non-porous powder, and is not limited in the shape, but is more preferably plate-shaped. Furthermore, the average particle size of the titanium oxide-containing powder is preferably 5 to 50 μm, and more preferably 10 to 40 μm.

When the titanium oxide-containing powder is a porous powder, the ability to remove sebum is enhanced. Further, the titanium oxide-containing powder also absorbs water, as the above-described porous powder does.

For the titanium oxide-containing powder, those described in, for example, JP-A-8-26931 or JP-A-2004-67500 can be used.

Among the titanium oxide-containing powders, plate-shaped porous silica containing titanium oxide is preferred because there occurs light scattering due to the difference between the refractive index of titanium oxide and that of silica, and thus it is possible to effectively make the unevenness of the skin hardly visible.

The titanium oxide-containing powder can be used solely or in combination of two or more species, and is preferably contained in an amount of 2 to 30% by weight, more preferably 5 to 20% by weight, and even more preferably 7 to 10% by weight, based on the total composition so that the skin after applying the preparation does not look so white, and sufficient effects of concealing unevenness can be obtained.

When the titanium oxide-containing powder is a porous powder, the sum of the weight of the above-mentioned porous powder and the weight of the titanium oxide-containing powder is preferably 5 to 40% by weight, and more preferably 10 to 30% by weight, based on the total composition of the cosmetic skin preparation.

According to the present invention, the cosmetic preparation may further contain another powder other than those mentioned above. The powder other than those mentioned above may be any of spherical-shaped, plate-shaped and amorphous. Such powder preferably has an average particle size of 0.001 to 30 μm.

The shape of the spherical powder is perfectly spherical, or similar to sphere. Examples of the spherical powder include inorganic powders of calcium silicate, magnesium silicate, silicic anhydride and the like; organic powders of crystalline cellulose, poly(meth)acrylic acid esters (methyl, ethyl esters), nylon powder, polyvinylpyrrolidone and the like; polymethylsilsesquioxane powders in which siloxane bonds extend three-dimensionally to form a network structure, and a methyl group is bound to one silicon atom to result in a structure having properties that are intermediate between inorganic and organic. The spherical powder preferably has an average particle size of 0.1 to 30 μm, and more preferably 1 to 20 μm. The spherical powder can be used in combination of one or more species, and is preferred because it can give a light dry sensation.

The plate-shaped powder may be exemplified by talc, mica, kaolin, sericite, pearl pigments, or the like. The plate-shaped powder preferably has an average particle size of 0.1 to 30 μm, and more preferably 1 to 20 μm. The plate-shaped powder can be used in combination of one or more species, and is preferred in view of good receptibility of cosmetic preparations, and good spreading.

Furthermore, the amorphous microparticle is preferably amorphous microparticulate silicic anhydride, and preferably has an average particle size of 0.001 to 0.01 μm, and more preferably 0.001 to 0.02 μm. Such microparticles are preferred because there are obtained a good sense of use with no occurrence of a sensation of straining, and good stability with no separation of oil components. The particle size of this amorphous microparticulate silicic anhydride is measured using a transmission electron microscope.

Examples of the amorphous microparticulate silicic anhydride include hydrophilic amorphous microparticulate silicic anhydride having a particle size in the above-mentioned range, which is obtained by hydrolyzing conventional silicon tetrachloride under a hydrogen-oxygen flame, and an amorphous microparticulate silicic anhydride obtained by hydrophobizing the surface of the hydrophilic amorphous microparticulate silicic anhydride. The amorphous microparticulate silicic anhydride may be either hydrophilic or hydrophobic, but is preferably hydrophilic.

For the amorphous microparticulate silicic anhydride, commercially available products such as Aerosil 200, Aerosil 300, Aerosil R972, Aerosil R974, Aerosil R202, Aerosil RY200 (all available from Nippon Aerosil Co., Ltd.), Taranox 500 (available from Tarco, Inc.), and the like may be used.

The amorphous microparticle silicic anhydride is preferably contained in an amount of 0.1 to 5% by weight, and more preferably 0.1 to 1% by weight, based on the total composition of the cosmetic skin preparation so that a good sense of use with no occurrence of a sensation of straining, and good stability with no separation of oil components are obtained, and an effect of well sustaining the makeup is obtained.

Such powder may be used solely or in combination of two or more species, and is preferably contained in an amount of 1 to 40% by weight, and more preferably 4 to 25% by weight, based on the total composition of the cosmetic skin preparation, from the viewpoints of the sense of use and the effect of obscuring the unevenness.

The total content of all of the powders including the porous powder (weight before absorbing water) is preferably 30 to 45% by weight, and more preferably 35 to 40% by weight, based on the total composition of the cosmetic skin preparation, from the viewpoint of stably maintaining water.

Furthermore, the content ratio (the weight ratio and the weights of the powders of both sides are based on weights before absorbing water) between the powders other than the porous powder, and the porous powder (in the case where the titanium oxide-containing powder is a porous powder, it is included in the porous powder) is preferably 2:5 to 3:4, from the viewpoint of a balance between the ability to remove sebum and the sense of use.

Moreover, according to the present invention, the powder surface of the powders used may be either hydrophilic or hydrophobic. The method of hydrophobizing treatment may be exemplified by trimethylsiloxation treatment using trimethylsilyl chloride, hexamethyldisilazane or the like; methylation treatment using dimethyldichlorosilane; coating/plating treatment using methylhydrogenpolysiloxane; coating with dimethylpolysiloxane, metal soaps and the like.

The average particle size of the powders used in the present invention represents a volume-average particle size (D4) (average particle size calculated on the basis of volume fraction). The measurement can be performed easily and reproducibly using a particle size distribution meter of laser diffraction type.

According to the present invention, the powders including the above-described porous powder are rendered to absorb water. The method of absorbing water is not limited, and the powders including the porous powder can be mixed with water, or with water containing other components, thus to absorb water. Alternatively, the powders including the porous powder may be mixed with a binder, and then mixed with water, or with water containing other components, thus to absorb water.

According to the present invention, it is preferable that the water absorbability of all of the powders including the porous powder (all of the powders being in a state before absorbing water) is 50 to 150 mL/100 g, and more preferably 70 to 130 mL/100 g, from the viewpoint of stable manufacturing without separation of water. The water absorbability is measured as described above.

According to the present invention, the binder to be coated on the surface of the porous powder contains a crosslinked type organopolysiloxane, and may be any material as long as it binds the powder particles when coated on the surface of the powder. However, specifically, the binder preferably contains a crosslinked type organopolysiloxane and an oily agent component which is liquid at 25° C.

According to the present invention, examples of the crosslinked type organopolysiloxane include crosslinked type alkylarylpolysiloxanes, and crosslinked type alkylpolysiloxanes. The crosslinked type alkylarylpolysiloxane may be exemplified by a crosslinked type organopolysiloxane having an alkyl group having 1 to 5 carbon atoms and an aryl group having 6 to 10 carbon atoms, and specific examples thereof include crosslinked type methylphenylpolysiloxane and the like. The crosslinked type alkylpolysiloxane may be exemplified by a crosslinked type dialkylpolysiloxane having an alkyl group having 1 to 5 carbon atoms, and specific examples thereof include crosslinked type dimethylpolysiloxane, crosslinked type methylphenylpolysiloxane, and the like.

Further examples of the crosslinked type organopolysiloxane that may be used include commercially available products such as paste-like KSG15, which is a mixture of decamethylcyclopentasiloxane and a crosslinked type organopolysiloxane; paste-like KSG16, which is a mixture of low-viscosity dimethylpolysiloxane and a crosslinked type organopolysiloxane; paste-like KSG18, which is a mixture of methylphenylpolysiloxane and crosslinked type methylphenylpolysiloxane (all of them available from Shin-Etsu Chemical Co., Ltd.).

The crosslinked type organopolysiloxane has an excellent ability to gelate oil and thus can impart desirable cosmetic properties without drying the skin. A composition obtained using this crosslinked type organopolysiloxane feels comfortable upon use, is soft, and is not sticky when touched. The softness is attributable partially to the organized structure of the crosslinked type organopolysiloxane, and partially to the properties comparable to a microsponge which traps oil.

The crosslinked type organopolysiloxane is preferably contained in an amount of 0.6 to 9% by weight, and more preferably 0.9 to 6.3% by weight, based on the total composition of the cosmetic skin preparation, from the viewpoint of the sense of use without stickiness.

Furthermore, the binder can contain alkyl-modified silicones, and thus can further improve the storage stability with regard to the suppression of oil oozing out from the container, and the like.

The alkyl-modified silicone is not limited as long as it is conventionally used in cosmetic preparations. The alkyl-modified silicone may be exemplified by dimethylpolysiloxane in which at least one silicon atom is substituted with an alkyl group having 6 to 24 carbon atoms, and which is represented by the following formula:

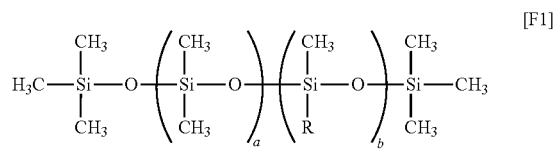

[F1]

wherein R represents an alkyl group having 6 to 24 carbon atoms; and a and b each represent a number from 50 to 1000.

The number average molecular weight of the alkyl modified silicone is preferably 10,000 to 1,000,000, and more preferably 10,000 to 500,000. Also, R in the formula is preferably an alkyl group having 16 to 22 carbon atoms.

The alkyl-modified silicone may be used solely or in combination of two or more species, and is preferably contained in an amount of 0.5 to 2% by weight, and more preferably 1% by weight, based on the total composition of the cosmetic skin preparation, from the viewpoints of having a good sense of use without stickiness and excellent stability.

Other oily agent components contained in the binder may include silicone oils, hydrocarbon oils, ester oils, ether oils, fluorine oils, and the like.

The silicone oil may be exemplified by a low molecular weight, straight-chained polyorganosiloxane represented by Formula (1), a low molecular weight, cyclic polysiloxane represented by Formula (2), or the like:

[F2]

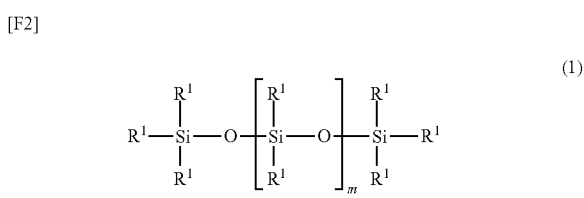

(1)

wherein $R^1$ represents an alkyl group having 1 to 5 carbon atoms, or an aryl group having 6 to 10 carbon atoms, provided that all of R's may be identical or different; and m represents a number from 0 to 100,000;

[F3]

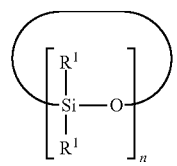

(2)

wherein $R^1$ has the same meaning as defined above; and n represents a number from 4 to 6.

The straight-chained organopolysiloxane may be exemplified by a straight-chained alkylpolysiloxane having an alkyl group having 1 to 5 carbon atoms, a straight-chained alkylarylpolysiloxane having an alkyl group having 1 to 5 carbon atoms and an aryl group having 6 to 10 carbon atoms. Specific examples thereof include straight-chained dimethylpolysiloxane, straight-chained methylphenylpolysiloxane. Among these straight-chained organopolysiloxanes, those having m of 0 to 100 (having a viscosity of 100 mm²/s or less) are preferred, and those having m of 2 to 50 are more preferred, from the viewpoint of the sense of touch.

The cyclic polysiloxane may be exemplified by a cyclic siloxane having an alkyl group having 1 to 5 carbon atoms as the substituent, and specific examples thereof include octamethylcyclotetrasiloxane, decamethylcyclopentasiloxane, and the like.

The hydrocarbon oil may be exemplified by liquid paraffin, squalane, light liquid isoparaffin, heavy liquid isoparaffin, polybutene, or the like.

Examples of the ester oil include plant oils such as safflower oil, soybean oil, grapeseed oil, sesame oil, wheat germ oil, avocado oil, olive oil, castor oil, macadamia nut oil, meadow form oil and the like; animal oils such as mink oil, turtle oil, liquid lanolin and the like; fatty acid esters of lower alcohols, such as isopropyl myristate, isopropyl isostearate, lanolin fatty acid isopropyl esters; fatty acid esters of higher alcohols, such as 2-ethylhexyl isononanoate, isotridecyl isononanoate, octyldodecyl myristate, octyldodecyl oleate, cetyl 2-ethylhexanoate, isocetyl 2-ethylhexanoate, isostearyl isostearate; oxyacid esters of higher alcohols, such as diisostearyl malate, cetyl lactate; fatty acid esters of polyhydric alcohols, such as glyceryl tricaprylate, glyceryl tri-2-ethylhexanoate, glyceryl triisostearate, glycerin tri(caprylate-caprate), propylene glycol dicaprylate, propylene glycol di(caprylate-caprate), propylene glycol diisostearate, neopentyl glycol dicaprate, neopentyl glycol 2-ethylhexanoate.

Examples of the ether oil include cetyl dimethylbutyl ether, while examples of the fluorine oil include perfluoropolyether, perfluorocarbon, and the like.

Such oily agent components may be used solely or in combination of two or more species, and is preferably contained in an amount of 35 to 60% by weight, and more preferably 40 to 55% by weight, based on the whole composition.

According to the present invention, more excellent effects can be obtained by using a crosslinked type organopolysiloxane, and a volatile silicone and/or a non-volatile liquid oil as the binder, and even more excellent effects can be obtained by using an alkyl-modified silicone.

In addition, according to the present invention, it is preferable for the binder not to contain moisture.

The content ratio (weight ratio) between all of the powders including the porous powder (all of the powders being in a state before absorbing water) and all of the binders is preferably 1:1 to 3:5, from the viewpoint of the sense of use.

The cosmetic skin preparation of the present invention may contain, in addition to the above-described components, semi-solid hydrocarbons, esters, fats and oils from animals and plants, higher fatty acids, higher alcohols; various polymer resins, polyhydric alcohols, moisturizers, ultraviolet ray absorbents, colorants, pearl agents, extender pigments, thickeners, surfactants, antioxidants, preservatives, intercellular lipids, vitamins, anti-inflammatory agents, perfumes, other drugs, and the like, depending on the purpose of use.

The cosmetic skin preparation of the present invention preferably contains water in an amount of 10 to 20% by weight, and more preferably 12 to 18% by weight, based on the total composition, from the viewpoints of the sense of touch when applied on the skin, and the water absorbability of the porous powder. By adding water, a refreshing sensation and a cooling sensation can be obtained.

The cosmetic skin preparation of the present invention can be prepared by, for example, mixing all of the powders including the porous powder, impregnating the powders with a certain portion or the entire amount of water, then adding oily agent components while kneading, and if necessary, adding additional water while kneading.

Also, when the cosmetic preparation is prepared by, preferably, rendering the powders to absorb water in advance, adding the binder containing a crosslinked type organopolysiloxane while kneading, and adding additional water in one or two or more portions while kneading, then a more stable cosmetic skin preparation can be obtained.

The amount of water that is absorbed by the powders in advance (hereinafter, referred to as water A) is preferably ⅔ to ¾ (weight ratio) of the total amount of water contained in the cosmetic skin preparation.

Furthermore, the water A is preferably mixed with the powders in an amount of 90 to 100% by weight of all of the powders contained in the cosmetic skin preparation, and absorbed by the powders. The method of absorbing water is not limited, and may be exemplified by a method of mixing powders in a Henschel mixer and then spraying the aqueous phase; a method of mixing all of the powders in a rocking mixer and then spraying the aqueous phase; a method of mixing the powders in a double-planetary mixer and then spraying the aqueous phase. The water A may have water-soluble components mixed and dissolved therein in advance.

Also, it is preferable for the powders to absorb all of the water A. Whether the water A has been all absorbed can be determined by, for example, checking with a tester that no electricity is being conducted therethrough.

Next, the binder is slowly added, and the resulting mixture is kneaded. The method of kneading is not limited, and may be exemplified by a method of kneading using a Henschel mixer or a double-planetary mixer. A crosslinked type organopolysiloxane may be mixed and dissolved in advance in the binder.

After mixing the binder, the additional water (hereinafter, referred to as water B) is added, and the resulting mixture is kneaded. The method of kneading is not limited, and may be exemplified by a method of kneading using a Henschel mixer or a double-planetary mixer. The water B may have water-soluble components mixed and dissolved therein in advance. Furthermore, it is possible to mix and disperse in advance a portion of the powders, particularly a portion of the porous powder (10% by weight or less, preferably 1 to 10% by weight, of all of the powders contained in the cosmetic skin preparation), in the water B. By adding the porous powder into the water B to be contained therein, it is possible to further suppress water separation after mixing, and also, the cooling sensation of the porous powder containing water is improved. It is preferable for the binder not to contain water and not to conduct electricity therethrough when checked with a tester.

It is possible to mix the entire amount of water in the cosmetic preparation with the entire amount of the powders all at once, but then, water may ooze out during the mixing with the oily agents. For this, a cosmetic skin preparation having more excellent stability with no water separation can be obtained by mixing the water in several portions. Also, from the viewpoint of stability as such, the total amount of water to be contained in the cosmetic skin preparation is preferably set to 30 to 70% of the water absorbability of all of the powders including the porous powder.

The cosmetic skin preparation of the present invention has the powder particles bound by the binder, thus having an appropriate viscosity while being capable of maintaining a constant form.

The cosmetic skin preparation of the present invention preferably has a viscosity, which is measured at 25° C. and at 5 rpm with a B8R type viscometer, of 100 to 4000 Pa·s, more preferably 300 to 3000 Pa·s, and even more preferably 500 to 2000 Pa·s.

The cosmetic skin preparation of the present invention has excellent effects of removing sebum and concealing unevenness.

EXAMPLES

Example 1

Cosmetic skin preparations having the compositions indicated in Table 1 were prepared by the method of preparation as described below, and were evaluated for the presence of spreading, receptibility, non-stickiness, no straining, light dryness, makeup sustainability and an effect of obscuring pores, upon use of the respective cosmetic preparations. The results are indicated together in Table 1.

(Method of Preparation)

While stirring the powders, the aqueous phase components are added. After rendering the powders to absorb all of the aqueous phase components and checking with a tester that no electricity is conducted therethrough, the oil phase components were added to this powder mixture, and the resulting mixture was kneaded to yield a cosmetic skin preparation. In addition, the resulting cosmetic skin preparation was also checked with a tester that no electricity is conducted therethrough.

(Method of Evaluation)

A sensory evaluation was performed by 10 expert panelists, for the presence of spreading, receptibility, non-stickiness, no straining, light dryness, makeup sustainability, an effect of obscuring pores and an overall assessment, upon use of the respective cosmetic preparations, on the basis of 5 grades from point 1 to point 5, and the average point was determined. Thus, the cosmetic preparation was judged on the basis of the following criteria.

A: average point of 4.5 to 5.0

B: average point of 3.5 to 4.4

C: average point of 2.5 to 3.4

D: average point of 1.5 to 2.4

E: average point of 1.0 to 1.4

TABLE 1

| | | Example Product | | | | Comparative Product | |
|---|---|---|---|---|---|---|---|
| | Component (wt %) | 1 | 2 | 3 | 4 | 1 | 2 |
| Powder component | Plate-shaped porous silica (Water absorbability: 74 mL/100 g, Average particle size 10 μm) | 9.0 | 9.0 | 10.0 | 9.0 | | 9.0 |
| | Spherical porous silica (Water absorbability: 168 mL/100 g, Average particle size 12 μm)[1] | 13.5 | 13.5 | 15.0 | 13.5 | — | 13.5 |
| | Silicone-treated microparticulate zinc oxide[1] | 3.0 | 3.0 | 3.0 | | 3.0 | 3.0 |
| | Methyl methacrylate cross polymer (Average particle size 17 μm)[2] | 5.0 | 5.0 | 4.0 | 5.0 | 5.0 | 5.0 |
| | Methylsiloxane network polymer (Average particle size 1 μm)[3] | 5.0 | 5.0 | 4.0 | 8.0 | 5.0 | 5.0 |
| | Amorphous microparticulate silicic anhydride A (Average particle size 12 nm)[4] | 0.5 | | 0.5 | | | |
| | Amorphous microparticulate silicic anhydride B (Average particle size 7 nm)[5] | | 0.5 | | 0.5 | | 0.5 |
| | Ethyl para-ethoxybenzoate | 0.2 | 0.2 | 0.2 | 0.2 | 0.2 | 0.2 |
| Binder component | Crosslinked type organopolysiloxane A[6] | 23.0 | | | 23.0 | 23.0 | |
| | Crosslinked type organopolysiloxane B[7] | | | 20.0 | | | |
| | Crosslinked type organopolysiloxane C[8] | | 20.0 | | | | |
| | Decamethylcyclopentasiloxane[9] | | | 8.0 | | | |
| | Dimethylpolysiloxane[10] | 12.0 | 13.0 | 5.0 | 12.0 | 23.0 | 22.0 |
| | Isotridecyl isononanoate[11] | 11.5 | | 13.0 | | 23.0 | |
| | Neopentyl glycol dicaprate[12] | | 13.0 | | | | 21.8 |
| | Dodecyl-1,3-dimethyl butyl ether | | | | 12.5 | | |
| | Alkyl-modified silicone[13] | 1.0 | 1.0 | 1.0 | | 1.0 | 1.0 |
| Aqueous phase | 55% Ethanol | 2.0 | 4.0 | 3.0 | 2.0 | 2.0 | 2.0 |
| | Purified water | Balance | Balance | Balance | Balance | Balance | Balance |
| | Total | 100 | 100 | 100 | 100 | 100 | 100 |
| | Water absorbability of all powders (mL/100 g) | 92 | 91.5 | 98 | 93 | 35 | 91.7 |
| | Viscosity (Pa · s) | 800 | 1000 | 1500 | 1250 | 0.5 | — |
| Evaluation | Spreading | A | B | A | A | B | B |
| | Receptibility | A | B | B | B | D | B |
| | Non-stickiness | A | A | A | A | E | C |
| | No straining | A | A | A | A | B | B |
| | Light dryness | B | A | A | A | E | C |

TABLE 1-continued

|  | Example Product | | | | Comparative Product | |
|---|---|---|---|---|---|---|
| Component (wt %) | 1 | 2 | 3 | 4 | 1 | 2 |
| Makeup sustainability | A | A | A | B | D | D |
| Effect of obscuring pores | A | A | A | A | E | E |
| Overall | A | A | A | A | D | C |

*[1] One treated with dimethylpolysiloxane up to 2% by weight
*[2] Matsumoto Microsphere M-503B (Matsumoto Yushi-Seiyaku Co., Ltd.)
*[3] KMP559 (Shin-Etsu Chemical Co., Ltd.)
*[4] Aerosil 200 (Nippon Aerosil Co., Ltd.)
*[5] Aerosil 300 (Nippon Aerosil Co., Ltd.)
*[6] Mixture of crosslinked type methylpolysiloxane and dimethylpolysiloxane (Crosslinked type ethylpolysiloxane:methylpolysiloxane = 25:75 (weight ratio)) (KSG16, Shin-Etsu Chemical Co., Ltd.)
*[7] Mixture of crosslinked type methylpolysiloxane and decamethylcyclopentasiloxane (crosslinked type methylpolysiloxane:decamethylcyclopentasiloxane = 6:94 (weight ratio)) (KSG15, Shin-Etsu Chemical Co., Ltd.)
*[8] Mixture of crosslinked type methylphenylpolysiloxane and methylphenylpolysiloxane (crosslinked type methylphenylpolysiloxane:decamethylcyclopentasiloxane = 15:85 (weight ratio)) (KSG18, Shin-Etsu Chemical Co., Ltd.)
*[9] SH245, Toray Dow Corning Silicone Co., Ltd.
*[10] Silicon KF-96A, 6 cs, Shin-Etsu Chemical Co., Ltd.
*[11] Salacos 913, Nisshin Oillio Group, Ltd.
*[12] Estemol N-01, Nisshin Oillio Group, Ltd.

*[13] 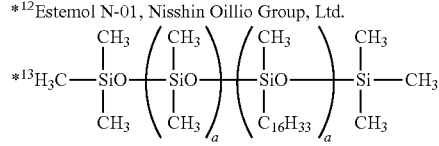

$a = b = 50 \sim 1000$

Number average molecular weight 10,000 to 500,000

Example 2

Cosmetic skin preparations having the compositions indicated in Table 2 were prepared in the same manner as in Example 1, and were likewise evaluated for the presence of spreading, receptibility, non-stickiness, no straining, light dryness, makeup sustainability and an effect of obscuring pores, upon use of the respective cosmetic preparations. The stability was also evaluated. The results are indicated together in Table 2.

(Method of Evaluating the Stability)

Each cosmetic preparation was filled in a tube (screw-capped) and was stored at 50° C. for 1 month. Then, when it was recognized that oil was oozing out from the mouth of the tube, it was graded "IN"; when none was recognized, it was graded "Y".

TABLE 2

|  | Component (wt %) | Example Product | | | Comparative Product |
|---|---|---|---|---|---|
|  |  | 5 | 6 | 7 | 3 |
| Powder component | Plate-shaped porous silica (Water absorbability: 74 mL/100 g, Average particle size 10 μm) | 9.0 | 9.0 | 10.0 |  |
|  | Spherical porous silica (Water absorbability: 168 mL/100 g, Average particle size 12 μm) | 13.5 | 13.5 | 15.0 |  |
|  | Spherical porous silica (Water absorbability: 150 mL/100 g, Average particle size 3 μm) |  |  |  | 10.0 |
|  | Spherical porous silica (Water absorbability: 300 mL/100 g, Average particle size 3 μm) |  |  |  | 3.0 |
|  | Silicone-treated microparticulate zinc oxide*[14] | 3.0 | 3.0 |  |  |
|  | Methyl methacrylate cross polymer (Average particle size 17 μm)*[2] | 5.0 | 5.0 | 4.0 |  |
|  | Methylsiloxane network polymer (Average particle size 1 μm)*[3] | 5.0 | 5.0 | 4.0 |  |
|  | Fluorine-treated methylsiloxane network polymer (Average particle size 1 μm) |  |  |  | 1.0 |
|  | Spherical silicone powder (Average particle size 4.5 μm)*[15] |  |  |  | 20.0 |
|  | Silicone-coated ultramarine blue pigment*[16] |  |  |  | 0.01 |
|  | Amorphous microparticulate silicic anhydride A (Average particle size 12 nm)*[4] | 0.5 |  | 0.5 |  |
|  | Amorphous microparticulate silicic anhydride B (Average particle size 7 nm)*[5] |  | 0.5 |  |  |
|  | Ethyl para-ethoxybenzoate | 0.2 | 0.2 | 0.2 | 0.1 |

TABLE 2-continued

|  | Component (wt %) | Example Product | | | Comparative Product |
|---|---|---|---|---|---|
|  |  | 5 | 6 | 7 | 3 |
| Binder component | Crosslinked type organopolysiloxane A*6 | 23.0 |  |  |  |
|  | Crosslinked type organopolysiloxane B*7 |  |  | 20.0 |  |
|  | Crosslinked type organopolysiloxane C*8 |  | 20.0 |  |  |
|  | Decamethylcyclopentasiloxane*9 |  |  | 8.0 |  |
|  | Methylcyclopolysiloxane*17 |  |  |  | 5.0 |
|  | Dimethylpolysiloxane*10 | 12.0 | 13.0 | 5.0 | 30.0 |
|  | Isotridecyl isononanoate*11 | 11.5 |  | 13.0 | 2.0 |
|  | Neopentyl glycol dicaprate*12 |  | 13.0 |  | 5.0 |
|  | Dodecyl-1,3-dimethyl butyl ether |  |  |  | 3.0 |
|  | 1-(2-Hydroxyethylamino)-3-isostearyloxy-2-propanol |  |  |  | 0.1 |
|  | Tris(ethoxyethoxyethyl) phosphate |  |  |  | 4.0 |
|  | Polyoxyethylene methylpolysiloxane*18 |  |  |  | 1.0 |
|  | Alkyl-modified silicone*13 | 1.0 | 1.0 | 1.0 |  |
| Aqueous phase | 86% Glycerin |  |  |  | 1.0 |
|  | 1,3-Butylene glycol |  |  |  | 4.0 |
|  | Dipropylene glycol |  |  |  | 1.0 |
|  | 55% Ethanol | 2.0 | 4.0 | 3.0 |  |
|  | Purified water | Balance | Balance | Balance | Balance |
|  | Total | 100 | 100 | 100 | 100 |
|  | Water absorbability of all powders (mL/100 g) | 92 | 91.5 | 89 | 180 |
|  | Viscosity (Pa · s) | 800 | 1000 | 1200 | 30 |
| Evaluation | Spreading | A | B | A | B |
|  | Receptibility | A | B | B | B |
|  | Non-stickiness | A | A | A | C |
|  | No straining | A | A | B | B |
|  | Light dryness | B | A | A | C |
|  | Makeup sustainability | A | A | A | D |
|  | Effect of obscuring pores | A | A | A | E |
|  | Stability | Y | Y | Y | N |

*14FINEX (Sakai Chemical Industry Co., Ltd.) treated with dimethylpolysiloxane up to 6% by weight
*15Tospearl 145A (Toshiba Silicone Co., Ltd.)
*16One treated with dimethylpolysiloxane up to 3% by weight.
*17SH244, Toray Dow Corning Silicone Co., Ltd.
*18SH3775M, Toray Dow Corning Silicone Co., Ltd.

Example 3

Cosmetic skin preparations having the compositions indicated in Table 3 were prepared in the same manner as in Example 1, and were likewise evaluated for the presence of spreading, receptibility, non-stickiness, no straining, light dryness, makeup sustainability and an effect of obscuring pores, upon use of the respective cosmetic preparations. The results are indicated together in Table 3.

TABLE 3

|  | Component (wt %) | Example Product | | | Comparative Product | |
|---|---|---|---|---|---|---|
|  |  | 8 | 9 | 10 | 4 | 5 |
| Powder component | Plate-shaped porous silica (Water absorbability: 74 mL/100 g, Average particle size 10 μm) | 9.0 | 9.0 | 10.0 |  |  |
|  | Spherical porous silica (Water absorbability: 168 mL/100 g, Average particle size 12 μm) | 13.5 | 13.5 | 15.0 |  |  |
|  | Silicone-treated microparticulate zinc oxide*14 | 3.0 | 5.0 | 10.0 |  | 10.0 |
|  | Methyl methacrylate cross polymer (Average particle size 17 μm)*2 | 5.0 | 5.0 | 4.0 | 5.0 | 8.0 |
|  | Methylsiloxane network polymer (Average particle size 1 μm)*3 | 5.0 | 5.0 | 4.0 | 5.0 | 7.0 |
|  | Amorphous microparticulate silicic anhydride A (Average particle size 12 nm)*4 | 0.5 |  | 0.5 |  | 0.5 |
|  | Amorphous microparticulate silicic anhydride B (Average particle size 7 nm)*5 |  | 0.5 |  |  |  |
|  | Ethyl para-ethoxybenzoate | 0.2 | 0.2 | 0.2 | 0.2 | 0.2 |

TABLE 3-continued

|  | Component (wt %) | Example Product | | | Comparative Product | |
|---|---|---|---|---|---|---|
|  |  | 8 | 9 | 10 | 4 | 5 |
| Binder component | Crosslinked type organopolysiloxane A*6 | 23.0 |  |  | 24.0 | 25.0 |
|  | Crosslinked type organopolysiloxane B*7 |  |  | 20.0 |  |  |
|  | Crosslinked type organopolysiloxane C*8 |  | 20.0 |  |  |  |
|  | Decamethylcyclopentasiloxane*9 |  |  | 8.0 |  |  |
|  | Dimethylpolysiloxane*10 | 12.0 | 12.0 | 5.0 | 24.0 | 18.0 |
|  | Isotridecyl isononanoate*11 | 11.5 |  | 10.0 | 24.0 | 17.0 |
|  | Neopentyl glycol dicaprate*12 |  | 12.0 |  |  |  |
|  | Alkyl-modified silicone*13 | 1.0 | 1.0 |  | 1.0 | 1.0 |
| Aqueous phase | 55% Ethanol | 2.0 | 3.0 | 1.0 | 2.0 | 2.0 |
|  | Purified water | Balance | Balance | Balance | Balance | Balance |
|  | Total | 100 | 100 | 100 | 100 | 100 |
|  | Water absorbability of all powders (mL/100 g) | 92.0 | 93.5 | 102.0 | 35.0 | 42.0 |
|  | Viscosity (Pa · s) | 800 | 1200 | 1350 | 0.5 | 15 |
| Evaluation | Spreading | A | B | B | B | B |
|  | Receptibility | A | B | A | D | C |
|  | Non-stickiness | A | A | A | E | E |
|  | No straining | A | A | B | B | C |
|  | Light dryness | B | A | A | E | E |
|  | Makeup sustainability | B | A | A | E | C |
|  | Effect of obscuring pores | B | B | A | D | D |
|  | Overall | A | A | A | D | D |

Example 4

Cosmetic skin preparations having the compositions indicated in Table 4 were prepared in the same manner as in Example 1, and were likewise evaluated for the presence of spreading, receptibility, non-stickiness, no straining, light dryness, makeup sustainability and an effect of obscuring pores, upon use of the respective cosmetic preparations. The results are indicated together in Table 4.

TABLE 4

|  | Component (wt %) | Example Product | | | | | Comparative Product |
|---|---|---|---|---|---|---|---|
|  |  | 11 | 12 | 13 | 14 | 15 | 6 |
| Powder component | Titanium oxide-containing, plate-shaped porous silica (Water absorbability: 75 mL/100 g, Average particle size 10 μm) | 9.0 | 9.0 | 10.0 | 9.0 |  |  |
|  | Titanium oxide-containing, plate-shaped non-porous silica (Water absorbability: 16 mL/100 g, Average particle size 10 μm) |  |  |  |  | 25.0 |  |
|  | Spherical porous silica (Water absorbability: 168 mL/100 g) | 13.5 | 13.5 | 15.0 | 13.5 | 5.0 |  |
|  | Silicon-treated microparticulate zinc oxide*14 | 3.0 | 3.0 | 3.0 |  |  | 3.0 |
|  | Methyl methacrylate cross polymer (Average particle size 17 μm)*2 | 5.0 | 5.0 | 4.0 | 5.0 | 5.0 | 5.0 |
|  | Methylsiloxane network polymer (Average particle size 1 μm)*3 | 5.0 | 5.0 | 4.0 | 8.0 | 5.0 | 5.0 |
|  | Amorphous microparticulate silicic anhydride A (Average particle size 12 nm)*4 | 0.5 |  | 0.5 |  | 0.5 |  |
|  | Amorphous microparticulate silicic anhydride B (Average particle size 7 nm)*5 |  | 0.5 |  | 0.5 |  |  |
|  | Ethyl para-ethoxybenzoate | 0.2 | 0.2 | 0.2 | 0.2 | 0.2 | 0.2 |
| Binder component | Crosslinked type organopolysiloxane A*6 | 23.0 |  |  | 23.0 | 23.0 | 23.0 |
|  | Crosslinked type organopolysiloxane B*7 |  |  | 20.0 |  |  |  |
|  | Crosslinked type organopolysiloxane C*8 |  | 20.0 |  |  |  |  |
|  | Decamethylcyclopentasiloxane*9 |  |  | 8.0 |  |  |  |
|  | Dimethylpolysiloxane*10 | 12.0 | 13.0 | 5.0 | 12.0 | 12.0 | 23.0 |
|  | Isotridecyl isononanoate*11 | 11.5 |  | 13.0 |  | 11.5 | 23.0 |
|  | Neopentyl glycol dicaprate*12 |  | 13.0 |  |  |  |  |
|  | Cetyl-1,3-dimethyl butyl ether |  |  |  | 12.5 |  |  |
|  | Alkyl-modified silicone*13 | 1.0 | 1.0 | 1.0 |  |  | 1.0 |

TABLE 4-continued

|  | Component (wt %) | Example Product | | | | | Comparative Product |
|---|---|---|---|---|---|---|---|
|  |  | 11 | 12 | 13 | 14 | 15 | 6 |
| Aqueous phase | 55% Ethanol | 2.0 | 4.0 | 3.0 | 2.0 | 1.0 | 2.0 |
|  | Purified water | Balance | Balance | Balance | Balance | Balance | Balance |
|  | Total | 100 | 100 | 100 | 100 | 100 | 100 |
|  | Water absorbability of all powders (mL/100 g) | 92.0 | 91.5 | 98.0 | 93.0 | 119.0 | 35.0 |
|  | Viscosity (Pa·s) | 800 | 1000 | 1500 | 1250 | 1350 | 0.5 |
| Evaluation | Spreading | A | B | A | A | B | B |
|  | Receptibility | A | B | B | B | A | D |
|  | Non-stickiness | A | A | A | A | A | E |
|  | No straining | A | A | A | A | B | B |
|  | Light dryness | B | A | A | A | A | E |
|  | Makeup sustainability | A | A | A | B | A | D |
|  | Effect of obscuring pores | B | B | A | B | A | D |
|  | Overall | A | A | A | A | A | D |

Example 5

Among the compositions indicated in Table 5, the powders except for 1% by weight of spherical porous silica were added to a Henschel mixer, and while stirring the powders, 79% by weight of all of the aqueous phase components were sprayed thereon to be absorbed by the powders. After checking with a tester that no electricity was conducted therethrough, the powder mixture was placed in a double-planetary mixer, and the entire amount of the binder components was added to the mixer while kneading. After completion of kneading, a liquid mixture in which 1% by weight of the spherical porous silica was dispersed in the remaining 21% by weight of the aqueous phase components, was added to the mixer while kneading to obtain a cosmetic skin preparation. In addition, the resulting cosmetic skin preparation was also checked with a tester that no electricity was conducted therethrough.

The viscosity of the resulting cosmetic skin preparation at 25° C. was 750 Pa·s. The cosmetic preparation was stable without water separation, and had excellent effects of removing sebum and concealing unevenness, and had an excellent cooling sensation.

Example 6

Among the compositions indicated in Table 5, all of the powders were added to a Henschel mixer, and while stirring the powders, 75% by weight of the aqueous phase components were sprayed thereon to be absorbed by the powders. After checking the mixture with a tester that no electricity was conducted therethrough, the powder mixture was placed in a double-planetary mixer, and the entire amount of the binder components were added thereto while kneading. After completion of kneading, the remaining 25% by weight of the aqueous phase components were added thereto while kneading to obtain a cosmetic skin preparation. The resulting cosmetic skin preparation was also checked with a tester that no electricity was conducted therethrough.

The viscosity of the resulting cosmetic skin preparation at 25° C. was 650 Pa·s. The cosmetic preparation was stable without water separation, and had excellent effects of removing sebum and concealing unevenness, and had an excellent cooling sensation.

TABLE 5

|  | Component (wt %) | Example | |
|---|---|---|---|
|  |  | 5 | 6 |
| Powder component | Plate-shaped porous silica (Water absorbability: 74 mL/100 g, Average particle size 10 μm) | 9.0 | 10.0 |
|  | Spherical porous silica (Water absorbability: 168 mL/100 g, Average particle size 12 μm) | 13.5 | 15.0 |
|  | Silicone-treated microparticulate zinc oxide[1] | 3.0 | 3.0 |
|  | Methyl methacrylate cross polymer (Average particle size 17 μm)[2] | 5.0 | 5.0 |
|  | Methylsiloxane network polymer (Average particle size 1 μm)[3] | 5.0 | 5.0 |
|  | Amorphous microparticulate silicic anhydride A (Average particle size 12 nm)[4] | 0.5 |  |
|  | Amorphous microparticulate silicic anhydride B (Average particle size 7 nm)[5] |  | 0.5 |
|  | Ethyl para-ethoxybenzoate | 0.2 | 0.2 |
| Binder component | Crosslinked type organopolysiloxane A[6] | 23.0 |  |
|  | Crosslinked type organopolysiloxane B[7] |  |  |
|  | Crosslinked type organopolysiloxane C[8] |  | 23.0 |
|  | Decamethylcyclopentasiloxane[9] |  |  |
|  | Dimethylpolysiloxane[10] | 12.0 | 12.0 |
|  | Isotridecyl isononanoate[11] | 11.5 |  |
|  | Neopentyl glycol dicaprate[12] |  | 11.5 |
|  | Alkyl-modified silicone[13] | 1.0 | 1.0 |

TABLE 5-continued

| | Component (wt %) | Example 5 | Example 6 |
|---|---|---|---|
| Aqueous phase | 55% Ethanol | 2.0 | 2.0 |
| | Purified water | Balance | Balance |
| | Total | 100 | 100 |
| | Water absorbability of all powders (mL/100 g) | 92 | 100 |
| | Viscosity (Pa · s, 25° C.) | 750 | 650 |

The invention claimed is:

1. A method of preparing a cosmetic skin preparation which comprises a powder component, a binder binding the powder particles and water, the method comprising rendering the powder component to absorb water in advance of adding a binder, next adding the binder while kneading, and having the powder particles bound by the binder,
wherein the powder component comprises a porous powder having an average particle size of 10 to 20 μm and an amorphous microparticulate silicic anhydride having an average particle size of 0.001 to 0.01 μm,
wherein the binder comprises a crosslinked type organopolysiloxane and an oily agent component which is liquid at 25° C., the weight ratio between the powder component before absorbing water, and the binder, is 1:1 to 3:5, and the powder component before absorbing water is present in an amount of 30 to 45% by weight and water is present in an amount of 10 to 20% by weight, based on the total composition of the cosmetic skin preparation.

2. The method according to claim 1, wherein the water absorbability of the powder component before absorbing water, is 50 to 150 mL/100 g.

3. The method according to claim 1, wherein the binder further contains alkyl-modified silicone.

4. The method according to claim 1, wherein the powder component further comprises a titanium oxide-containing silica powder.

5. The method according to claim 1, wherein the cosmetic preparation has a capability for the removal of sebum or concealment of unevenness.

6. The method according to claim 1, wherein the amount of the water to be absorbed by the powder in advance is ⅔ to ¾, by weight ratio, of the total amount of water contained in the cosmetic skin preparation.

7. The method according to claim 1, wherein the total amount of water contained in the cosmetic skin preparation corresponds to 30 to 70% of the water absorbability of the powder component.

8. The method according to claim 1, wherein the viscosity of the cosmetic skin preparation at 25° C. is 100 to 4000 Pa·s.

9. The method according to claim 1, comprising further adding a portion of water while kneading after rendering the powder component to absorb water in advance and adding the binder while kneading.

10. The method according to claim 1, wherein the porous silica is spherical-shaped or plate-shaped or both shapes in combination.

11. The method according to claim 1, wherein the powder component additionally comprises at least one non-porous powder, and the ratio between the total amount of non-porous powder to the total amount of porous powder is 2:5 to 3:4.

12. The method according to claim 1, wherein the crosslinked type organopolysiloxane is selected from the group consisting of a mixture of decamethylcyclopentasiloxane and a crosslinked type organopolysiloxane; a mixture of low-viscosity dimethylpolysiloxane and a crosslinked type organopolysiloxane; and a mixture of methylphenylpolysiloxane and crosslinked type methylphenylpolysiloxane.

13. The method according to claim 1, wherein the porous powder is contained in an amount of 5 to 40% by weight, and the amorphous microparticulate silicic anhydride is contained in an amount of 0.1 to 5% by weight, based on the total composition of the cosmetic skin preparation.

14. The method according to claim 1, wherein the porous powder comprises a porous silica having a water absorbability of 50 to 200 mL/100 g.

15. A method of preparing a cosmetic skin preparation which comprises a powder component, a binder binding the powder particles and water, the method comprising adding water to the powder component in advance of adding a binder to render the powder component to absorb all of water, next adding the binder while kneading, and having the powder particles bound by the binder,
wherein the powder component comprises a porous powder having an average particle size of 10 to 20 μm and an amorphous microparticulate silicic anhydride having an average particle size of 0.001 to 0.01 μm,
wherein the binder comprises a crosslinked type organopolysiloxane and an oily agent component which is liquid at 25° C., the weight ratio between the powder component before absorbing water, and the binder, is 1:1 to 3:5, and the powder component before absorbing water is present in an amount of 30 to 45% by weight and water is present in an amount of 10 to 20% by weight, based on the total composition of the cosmetic skin preparation.

16. The method according to claim 15, wherein the method comprises adding water to the powder component in advance of adding the binder to render the powder component to absorb all of water, next checking with a tester that no electricity is conducted therethrough, and then adding the binder while kneading.

17. The method according to claim 16, wherein the resulting cosmetic skin preparation is checked with a tester that no electricity is conducted therethrough.

18. The method according to claim 1, wherein the oily agent component contains dimethylpolysiloxane.

19. The method according to claim 1, wherein the porous powder is a porous silica containing titanium oxide.

20. The method according to claim 1, wherein the porous powder is a plate-shaped porous silica containing titanium oxide.

* * * * *